United States Patent
Simhambhatla et al.

(10) Patent No.: US 6,875,197 B1
(45) Date of Patent: Apr. 5, 2005

(54) DIMENSIONALLY STABLE AND GROWTH CONTROLLED INFLATABLE MEMBER FOR A CATHETER

(75) Inventors: Murthy V. Simhambhatla, San Jose, CA (US); Robert P. Saltman, Redwood City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 60 days.

(21) Appl. No.: 09/713,384

(22) Filed: Nov. 14, 2000

(51) Int. Cl.[7] .................. A61M 29/00; A61M 31/00; A61M 37/00

(52) U.S. Cl. ............... 604/96.01; 604/99.01; 604/103.06; 604/103.08

(58) Field of Search .................. 604/93.01, 95.01, 604/95.03, 96.01, 97.01–99.01, 102.01–102.03, 103, 103.01–103.13; 264/514, 515, 171.26, 171.27, 171.28

(56) References Cited

U.S. PATENT DOCUMENTS

| | | | |
|---|---|---|---|
| 4,113,594 A | | 9/1978 | Nyberg .................. 204/159.15 |
| 4,444,816 A | | 4/1984 | Richards et al. .............. 428/36 |
| 4,456,000 A | | 6/1984 | Schjeldahl et al. ......... 128/1 D |
| 4,871,810 A | * | 10/1989 | Saltman ...................... 525/133 |
| 5,091,478 A | * | 2/1992 | Saltman ...................... 525/166 |
| 5,108,370 A | * | 4/1992 | Walinsky ............... 604/102.02 |
| 5,250,228 A | * | 10/1993 | Baigrie et al. .............. 219/541 |
| 5,312,356 A | * | 5/1994 | Engelson et al. ...... 604/164.13 |
| 5,317,061 A | * | 5/1994 | Chu et al. .................... 525/199 |
| 5,318,587 A | * | 6/1994 | Davey ................... 604/103.14 |
| 5,382,384 A | * | 1/1995 | Baigrie et al. .............. 219/541 |
| 5,397,307 A | | 3/1995 | Goodin ........................ 604/96 |
| 5,456,666 A | * | 10/1995 | Campbell et al. ...... 604/103.08 |
| 5,458,572 A | * | 10/1995 | Campbell et al. ...... 604/103.08 |
| 5,470,314 A | * | 11/1995 | Walinsky ................ 604/103.11 |
| 5,478,319 A | * | 12/1995 | Campbell et al. ............ 264/520 |
| 5,484,411 A | * | 1/1996 | Inderbitzen et al. ... 604/103.08 |
| 5,554,120 A | * | 9/1996 | Chen et al. .................. 525/166 |
| 5,565,523 A | * | 10/1996 | Chen et al. .................. 525/176 |
| 5,733,496 A | | 3/1998 | Avellanet |
| 5,747,591 A | * | 5/1998 | Chen et al. .................. 525/176 |
| 5,759,172 A | * | 6/1998 | Weber et al. ........... 604/103.07 |

(Continued)

FOREIGN PATENT DOCUMENTS

| | | |
|---|---|---|
| EP | 0 540 858 A1 | 5/1993 |
| EP | 0 669 143 A1 | 8/1995 |
| EP | 0 737 488 A1 | 10/1996 |
| EP | 0 872 258 A2 | 10/1998 |
| WO | WO 95/17223 A1 * 6/1995 | .......... A61M/25/00 |

*Primary Examiner*—Henry Bennett
*Assistant Examiner*—Andrea M. Ragonese
(74) *Attorney, Agent, or Firm*—Fulwider Patton Lee & Utecht LLP

(57) ABSTRACT

A dimensionally stable and growth controlled inflatable member formed by adding a multifunctional agent to a soft polymer to form a compound, extruding an inflatable member from the compound, and crosslinking the compound. The inflatable member is configured to be formed-in-place with a body lumen. Preferably, the inflatable member is blown to a working diameter prior to use and then heated to the glass transition temperature of the polymer to shrink the diameter of the blown inflatable member back to about the nominal diameter of the tubing. In another embodiment, the invention is a dimensionally stable and growth controlled inflatable member comprising longitudinal zones of crosslinked material symmetrically spaced about the circumference of the inflatable member and a uniform working diameter. Preferably, there are three or more longitudinal zones that run the working length of the inflatable member. The selectively irradiated inflatable members are formed in a mold having symmetrically spaced longitudinal windows.

6 Claims, 3 Drawing Sheets

U.S. PATENT DOCUMENTS

| | | | |
|---|---|---|---|
| 5,792,300 A | | 8/1998 | Inderbitzen et al. ... 156/244.13 |
| 5,797,877 A | * | 8/1998 | Hamilton et al. ........... 604/264 |
| 5,849,846 A | * | 12/1998 | Chen et al. ................. 525/166 |
| 6,013,728 A | * | 1/2000 | Chen et al. ................. 525/166 |
| 6,024,722 A | * | 2/2000 | Rau et al. ................... 604/524 |
| 6,086,556 A | * | 7/2000 | Hamilton et al. ........... 604/523 |
| 6,090,099 A | * | 7/2000 | Samson et al. ............. 604/527 |
| 6,129,706 A | * | 10/2000 | Janacek ................ 604/103.08 |
| 6,190,357 B1 | * | 2/2001 | Ferrari et al. .......... 604/102.01 |
| 6,270,522 B1 | * | 8/2001 | Simhambhatla et al. .... 606/194 |
| 6,336,936 B2 | * | 1/2002 | Simhambhatla et al. ... 623/1.11 |
| 6,428,506 B1 | * | 8/2002 | Simhambhatla et al. . 604/96.01 |
| 6,592,550 B1 | * | 7/2003 | Boatman et al. ....... 604/103.06 |
| 6,596,818 B1 | * | 7/2003 | Zamore ...................... 525/426 |
| 2002/0077418 A | * | 12/1999 | Chen et al. .................... 525/88 |
| 2001/0027329 A1 | * | 6/2001 | Simhambhatla et al. .... 606/194 |
| 2002/0062133 A1 | * | 5/2002 | Gilson et al. ................ 606/200 |
| 2002/0103455 A1 | * | 8/2002 | Zhang et al. ............ 604/96.01 |

* cited by examiner

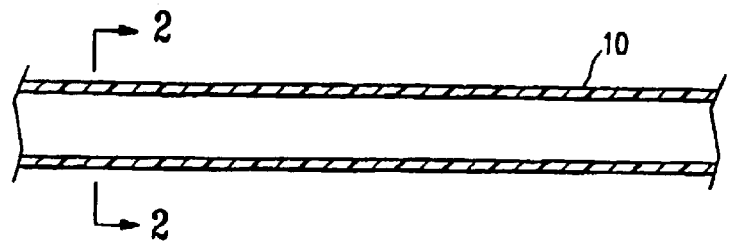
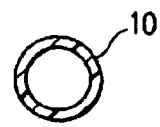
FIG. 1      FIG. 2
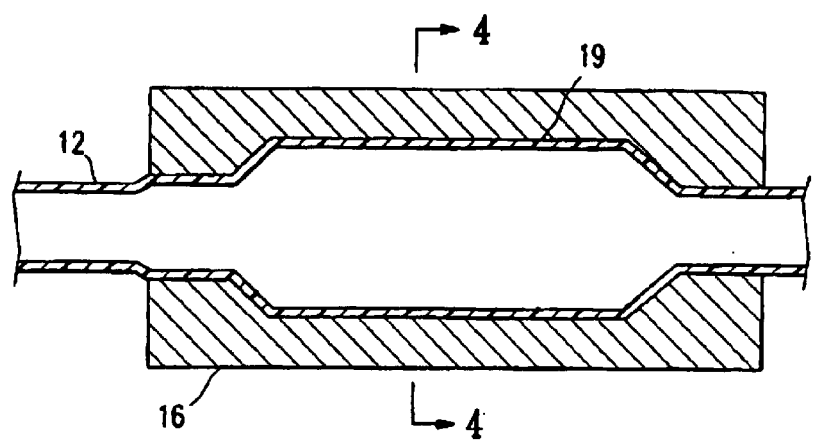
FIG. 3
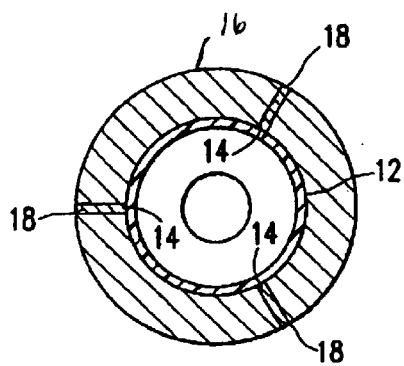
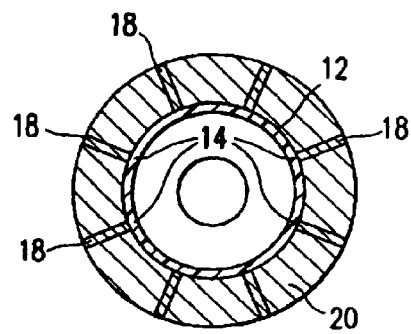
FIG. 4      FIG. 5

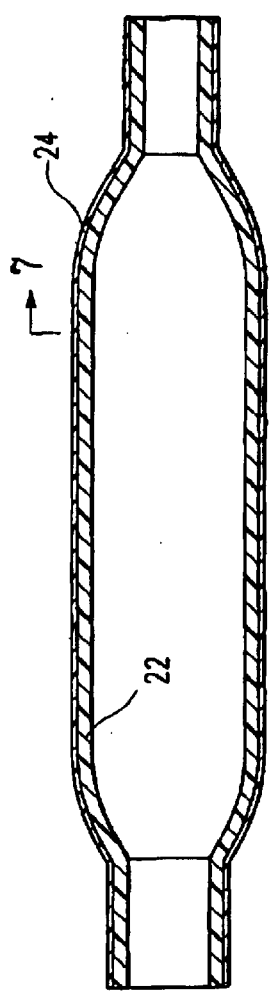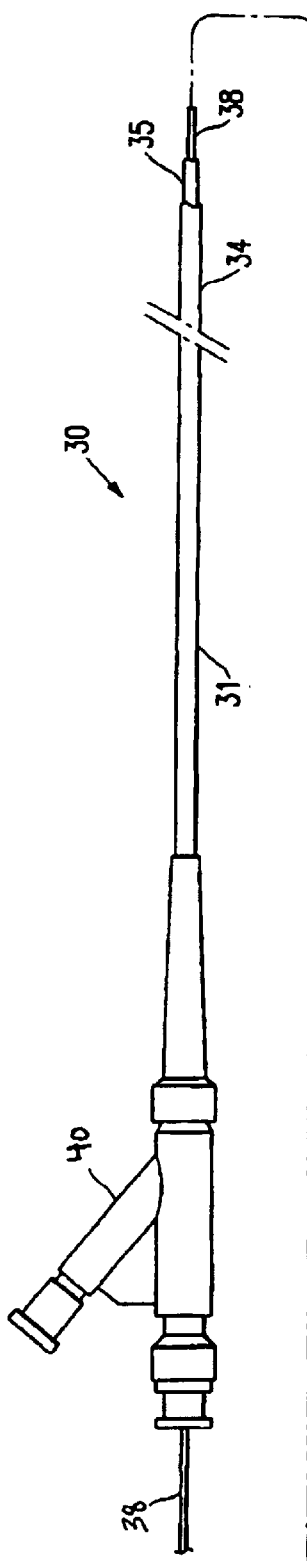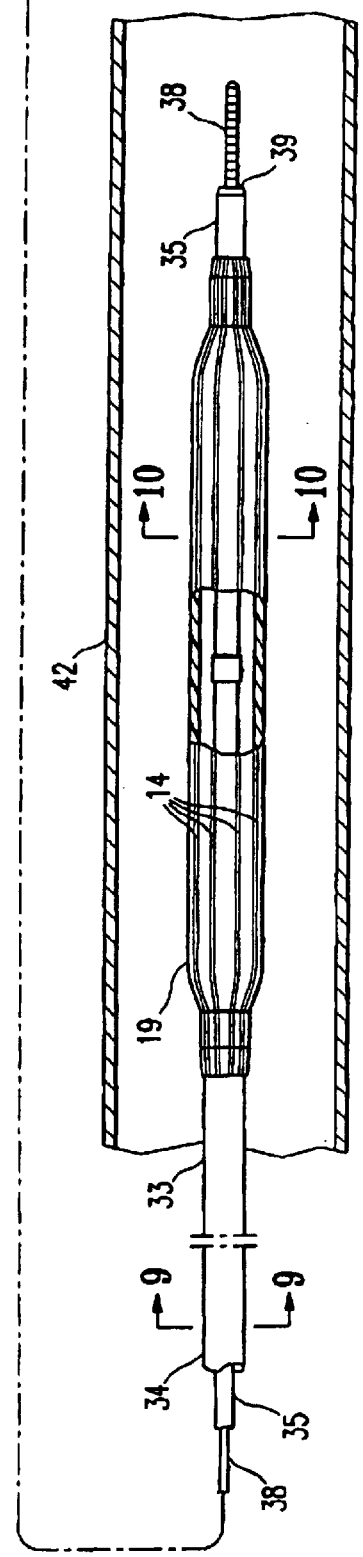

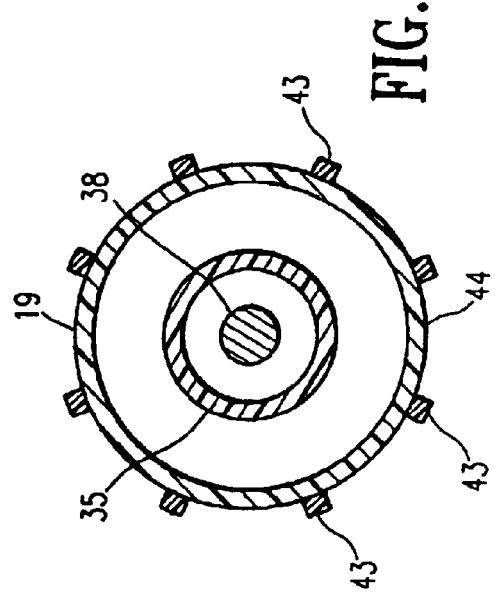
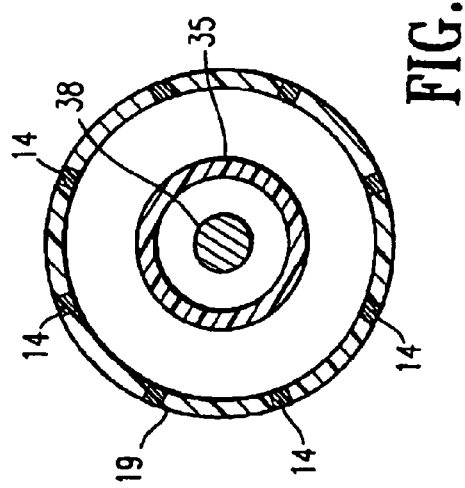
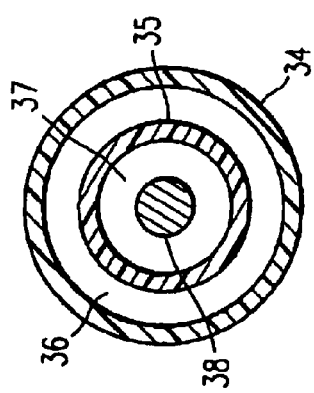

DIMENSIONALLY STABLE AND GROWTH CONTROLLED INFLATABLE MEMBER FOR A CATHETER

BACKGROUND OF THE INVENTION

This invention generally relates to the field of medical devices, and particularly to a catheter balloon formed at least in part of a crosslinked material.

In the design of balloons for catheters, and particularly angioplasty catheters, important considerations include controlling the expanded dimensions of the balloon and obtaining acceptable rupture characteristics. Further, the characteristics generally must be weighed against the softness, or feel, of the balloon. Although a soft feel can be desirable, compliance must be regulated to maintain sufficient control over balloon dimension. Likewise, acceptable rupture characteristics are critical to minimize the risk of catastrophic balloon failure.

Prior art techniques for producing balloons from soft materials with acceptable balloon rupture characteristics and low compliance have blow molded the balloons using high blow up ratios (BURs). The BUR is defined as the outer diameter of the balloon divided by the inner diameter of the balloon tubing used to form the balloon. One difficulty has been that polymer films have a limited biaxial stretch ratio beyond which the films suffer from defects such as microtears. Thus, balloons formed from softer materials that have been imbued with controlled radial growth through the use of high BURs must therefor not experience excessive axial stretching during formation or inflation. This typically results in a tradeoff between axial growth and radial growth in softer materials.

Control over these characteristics is especially important when designing formed-in-place balloons. In these catheters, the balloon is expanded within the patient's vessel from its nominal diameter, rather than introduced into the patient's vasculature as a deflated balloon formed by blow molding. Safety considerations require that these balloons be capable of reaching their rated nominal diameter at relatively low pressure, preferably less than about 15 atmospheres (atm). Thus, formed-in-place balloons must be compliant up to the desired working diameter and exhibit minimal compliance beyond the working diameter. Without these characteristics, the risk of damage to the vessel due to over expansion is considerable. EP 540858A1 discloses a method of making a formed-in-place balloon having elastic expansion within a limited pressure range, in which the balloon tubing is subjected to a heat treatment before being expanded and heat shrunk to the balloon tubing diameter to form the balloon.

Accordingly, there is a need for catheter balloons that offer improved dimensional stability. It would be a significant advance to provide balloons with improved radial compliance to a working diameter and low compliance beyond that dimension, and balloons that are configured to prevent excessive axial growth upon inflation. There is a corresponding need for balloon fabrication techniques that produce balloons having these characteristics. This invention satisfies these and other needs.

SUMMARY OF THE INVENTION

The invention is generally directed to dimensionally stable and growth controlled inflatable members for use with a catheter.

One embodiment comprises an inflatable member formed by the process comprising adding a multifunctional agent to a soft polymer to form a compound, extruding or otherwise forming an inflatable member from the compound, and cross-linking the compound of the extruded inflatable member. The inflatable member exhibits radial compliance to a desired working diameter within a first pressure range, and lower radial compliance above the first pressure range. Preferably, the resulting inflatable member exhibits radial compliance at inflation pressures of less than about 20 atm to a desired working diameter. The inflatable member is configured to be formed-in-place with a body lumen. Since the inflatable member retains its nominal balloon tubing diameter until it is inflated, catheters equipped with these inflatable members have relatively small profiles, facilitating insertion and the crossing of lesions. By tailoring the choice of polymer, the blend of multifunctional additive, and the amount of crosslinking, inflatable member can be configured to exhibit a desired compliance as it is blown through a pressure range from the nominal diameter of the tubing to its desired working diameter. However, once the working diameter is achieved, the crosslinking acts to restrain further radial growth. This helps prevent the inflatable member from causing damage to the body lumen by being overexpanded inadvertently. The invention also comprises the method for forming such inflatable members. The invention may further comprise such inflatable members that have been blown to the desired working diameter before being placed in the body lumen, and then heated to an elevated temperature, which in a presently preferred embodiment is the glass transition temperature of the polymer, to shrink the diameter of the blown inflatable member back to about the nominal diameter of the tubing for positioning and inflation within the body lumen. Upon reinflation within the body lumen, it reaches its nominal or working diameter at pressures less than, and preferably significantly less than the rated burst pressure of the inflatable member.

Another embodiment is directed to an inflatable member having zones of stiffening material spaced about the circumference of at least a section of the inflatable member. The zones generate an inflatable member that exhibits low axial compliance. Specifically, the zones have a higher modulus than the non-crosslinked portions of inflatable member, and limit axial growth of the inflatable member during inflation thereof without significantly affecting radial expansion. The stiffening zones expand with adjacent portions of the balloon such that the balloon section expands to a substantially cylindrical configuration. In one embodiment, the stiffening zones comprise polymeric material coextruded as a layer of the balloon, wherein the zones are coextruded onto a balloon formed of a softer material than the zones. In another embodiment, the stiffening zones comprise crosslinked polymeric material. In a presently preferred embodiment, the zones extend within only the working length of the inflatable member. However, in other embodiments, the zones may extend over less than the working length or over the entire length of the inflatable member. In one embodiment, the zones are longitudinally extending stripes axially aligned with the longitudinal axis of the inflatable member. However, the zones may have a variety of suitable configurations. Preferably, there are three or more zones.

One embodiment comprises a method for forming inflatable members with longitudinal crosslinked zones generally comprising blending a soft polymer with a multifunctional agent to form a compound, extruding or otherwise forming a tubular member, or parison, from the compound, blowing the parison into the inflatable member in a mold having longitudinal windows transparent to the crosslinking radiation, and crosslinking the compound with radiation.

Alternatively, the parison can be blown in a conventional mold and then reinflated in a second mold having longitudinal windows for crosslinking. In another embodiment, the method comprises providing an inflatable member, coating the inflatable member with crosslinkable material, selectively radiating or otherwise crosslinking longitudinal zones of the inflatable member, preferably by inflating the inflatable member in a mold having longitudinal windows transparent to crosslinking radiation, and then radiating the coated inflatable member. In certain embodiments, it may be desirable to remove the multifunctional agent from the areas of the inflatable member that are not exposed to radiation.

The terminology "soft polymers" used herein should be understood to mean polymers having a tensile modulus of typically less than about 125,000 psi, and preferably less than about 75,000 psi. Typically, the soft polymers used in the invention comprise polymers having a glass transition temperature of about 20° C. to about 60° C., and more specifically up to about 37° C. to about 40° C. Suitable polymers exhibit a relatively low flexural or tensile modulus, a relatively high tensile strength of not less than about 4000 psi, and a relatively high elongation to break of greater than about 200%. The Shore durometer hardness of the soft polymer is typically not greater than about 70D. Specific examples include polyamide-ether block copolymer (PEBAX), polyether-ester block copolymer, polyester-ester block copolymer, polyester-urethane block copolymer, polyolefin, polyolefin block copolymer, polyether-urethane block copolymer, polycarbonate-urethane copolymer, polyether-urethane, ethylene copolymers, polydimethyl siloxane (poly DMS), polysiloxanes and their block copolymers, vinylidene fluoride copolymers, EPDM, Santoprene, Kraton, and Viton. Absent the multifunctional agent, these soft polymers would not crosslink appreciably when exposed to crosslinking radiation, excepting polymers such as ethylene containing polymers including polyolefins which are crosslinkable by e-beam or gamma radiation. Preferably, the multifunctional agents include monomers and oligomers known in the art as crosslinking agents. Specific examples include multifunctional acrylates, vinylics, acetylenics, photopolymers, trimethylolpropane triacrylate (TMPTA), tripropyleneglycol diacrylate (TPGDA), triallyl cyanurate (TAC), triallyl isocyanurate (TAIC) and N,N'-m-phenylenediamaleimide.

The invention provides catheter balloons with a desired softness and improved expansion characteristics due to crosslinking or coextrusion which provides for controlled axial or radial expansion. These and other advantages will become more apparent from the following detailed description and exemplary figures.

BRIEF DESCRIPTION OF THE DRAWINGS

FIG. 1 is a longitudinal cross-sectional view of an inflatable member embodying features of the invention, which is crosslinked and configured to be formed-in-place.

FIG. 2 is a transverse cross-sectional view of the inflatable member shown in FIG. 1 taken along lines 2—2.

FIG. 3 is a longitudinal cross-sectional view of a balloon mold having longitudinal windows useful in the practice of a method which embodies features of the invention.

FIG. 4 is a transverse cross-sectional view of the mold shown in FIG. 3 taken along lines 4—4, illustrating an embodiment that comprises three windows which are transparent to crosslinking radiation.

FIG. 5 is a transverse cross-sectional view of the mold shown in FIG. 3, illustrating an alternative embodiment that comprises eight windows which are transparent to crosslinking radiation.

FIG. 6 is a longitudinal cross-sectional view of an inflatable member embodying features of the invention, which is coated with crosslinkable material.

FIG. 7 is a transverse cross-sectional view of the inflatable member shown in FIG. 6, taken along lines 7—7.

FIG. 8 is an elevational view, partially in section, of a balloon catheter embodying features of the invention having longitudinally extending stiffening sections.

FIG. 9 is a transverse cross-sectional view of the balloon catheter shown in FIG. 8 taken along lines 9—9.

FIG. 10 is a transverse cross-sectional view of the balloon catheter shown in FIG. 8 taken along lines 10—10.

FIG. 11 is a transverse cross-sectional view of the balloon catheter shown in FIG. 8 taken along lines 11—11 illustrating an alternative embodiment having stiffening zones comprising a coextruded outer layer of material.

DETAILED DESCRIPTION OF THE INVENTION

FIG. 1 shows a formed-in-place inflatable member 10 embodying features of the invention, configured to be blown to its working diameter within a body lumen. Inflatable member 10 is fabricated by blending a soft polymer with a multifunctional additive to form a compound. The compound then can be extruded conventionally into tubing. The tubing is then exposed to crosslinking radiation before being expanded into a balloon. FIG. 2 illustrates a transverse cross-sectional view of the inflatable member 10 shown in FIG. 1 taken along lines 2—2. Preferably, the inflatable member is configured so that it is compliant and may be expanded to its desired working diameter at relatively low inflation pressures, such as about 4 atm to about 12 atm. The inflatable member thus formed exhibits compliant radial expansion as it is expanded from the tubing diameter to the desired working diameter within a first pressure range, and substantially less expansion, such as noncompliant or semicompliant radial expansion, as it is expanded beyond the working diameter at a pressure above the first pressure range. The compliant radial expansion is generally about 0.03 mm/atm to about 0.10 mm/atm from about 3 atm to about 10 atm, and the noncompliant or semicompliant radial expansion is generally about 0.01 mm/atm to about 0.03 mm/atm from 10 atm to 25 atm, or from about nominal pressure to about rated burst pressure for a 3 mm outer diameter balloon.

To optimize the performance of inflatable member 10, it may be desirable to blow the crosslinked tubing to its working diameter prior to use in a patient. The tubing is blown in a mold similar to mold 16 illustrated in FIG. 3 and discussed below, except without longitudinally extending windows 18. The expanded inflatable member then may be heated to the glass transition temperature of the polymer to cause it to return to the nominal diameter of the tubing. This process can be repeated if necessary to condition the inflatable member so that it reliably blows to the desired working diameter and shape. The shape of the tubing can also be specially shaped, such as by selectively altering the wall thickness, to improve the blowing characteristics.

In an alternative embodiment illustrated in FIGS. 3–11, the balloon of the invention has longitudinally extending stiffening zones, so that axial growth of the inflatable member during inflation thereof is limited.

FIGS. 3–5 illustrate an embodiment of the invention comprising a preformed, selectively irradiated inflatable member 12 that has radially-spaced longitudinal zones 14 of crosslinked material. Inflatable member 12 is shown after being blown in mold 16. The parison for inflatable member 12 is formed by mixing the soft polymer with a multifunctional agent and then extruding a tubing from the resulting compound. The tubing is placed in mold 16 and inflation fluid is introduced to its interior to expand the tubing into the desired shape of the inflatable member. As shown in the cross-sectional view of FIG. 4, mold 16 is equipped with windows 18 that are transparent to the crosslinking radiation to form zones 14 at the portions of the inflatable member which are adjacent to the windows 18. The irradiation mold is formed of a material such as metal which is opaque to radiation. Windows 18 are open or are formed of a material transparent to radiation such as, for example, glass or quartz for ultraviolet radiation, titanium for e-beam radiation, and lead, gold, platinum, or iridium for gamma radiation. Preferably, mold 16 has three or more windows 18, which longitudinally extend at least the length of the section 19 of the mold corresponding to the working length of the balloon, and in one embodiment extend the entire length of the mold. FIG. 5 shows an alternate embodiment, wherein mold 20 has eight windows 18.

Mold 16 or 20 with inflated inflatable member 12 is exposed to crosslinking radiation either by rotating the mold in front of the radiation source or by employing a circular radiation source to ensure that each window 18 is evenly irradiated. An alternative method of forming inflatable member 12 includes blowing the tubing in a conventional mold, deflating the inflatable member and placing it in mold 16 or 20. Inflatable member 12 then is reinflated and selectively exposed to crosslinking radiation through apertures or windows 18.

Longitudinal zones 14 are circumferentially spaced about the inflatable member, and in a presently preferred embodiment are symmetrically spaced about the circumference of inflatable member 12. The crosslinked zones radially inflate with the noncrosslinked portions of the inflatable member at least up to the working diameter, so that a generally cylindrical shape is formed upon inflation, with a uniform working diameter along the working length of the inflatable member, as illustrated in FIGS. 3 and 4. Preferably, inflatable member 12 is formed from a soft polymer and is blown to a high BUR of about 4 to about 8, preferably about 6 to about 8. The crosslinked longitudinal zones 14 limit axial growth of the balloon to about 5% to about 10% of the original uninflated working length of the inflatable member (i.e., blown tubing), at the rated burst pressure of the inflatable member.

In the alternative embodiment shown in FIG. 6, selectively irradiated inflatable member 22 is uniformly coated with a cross linkable material 24 such as a multifunctional acrylate oligomer, di- and tri-vinyl benzene prepolymer or monomer, diallyl phthalate, photoresist, and sensitizers such as quinones. The coated inflatable member 22 is then placed within a windowed mold, such as shown in FIGS. 3–5, and irradiated. Alternatively, a parison is coated with crosslinkable material, blown in a mold having symmetrically spaced longitudinal windows and then irradiated to control axial growth. FIG. 7 illustrates a transverse cross-sectional view of the inflatable member 22 shown in FIG. 6 taken along lines 7—7.

FIGS. 8–10 illustrate a balloon catheter 30 embodying features of the invention, having an elongated catheter shaft 31 with an inflatable member 19 of the invention on a distal portion 33 of the shaft. In the embodiment illustrated, the inflatable member 19 has eight longitudinal zones stiffening zones 14 of crosslinked or coextruded material. The zones 14 would not necessarily be visible on the inflatable member 19, but are shown in FIG. 8 as lines 14 for illustrative purposes. The catheter shaft, illustrated in more detail in FIGS. 9 and 10, has an outer tubular member 34, and an inner tubular member 35 disposed within the outer tubular member and defining therewith annular lumen 36 which is in fluid communication with the interior of the inflatable member 19. The inner tubular member has an inner lumen 37 configured to slidably receive a guidewire 38, which extends to the port 39 in the distal end of the inner tubular member, as best illustrated in FIGS. 9 and 10, illustrating transverse cross sections of the catheter 30 taken along lines 9—9 and 10—10, respectively. An adapter 40 is mounted on the proximal end of the catheter shaft. In FIG. 8, the catheter 30 is illustrated in the patient's body lumen 42. To the extent not previously described herein, the −15 various catheter components may be formed of conventional materials. Although the embodiment illustrated in FIG. 8 has inflatable member 19 having longitudinal zones of stiffening material, inflatable members 10 or 22, as discussed above, would similarly be provided on distal end of catheter 30.

In the embodiment illustrated in FIG. 10, balloon 19 is formed of uniform, blended material where stiffening zones 14 are crosslinked material integral with adjoining portions of the balloon making up the balloon wall. FIG. 11 illustrates an alternative embodiment of inflatable member 19 in which stiffening zones comprise a coextruded outer layer 43 of stiffer material on layer 44. Although illustrated as an outer layer, the coextruded stiffening zones could be an inner layer of the inflatable member 19. Because the coextruded stiffening zones 43 are formed of a stiffer material than the layer 44, crosslinking is not required for coextruded stiffening zones 43 to limit axial growth of the inflatable member during inflation thereof. Preferably, the coextruded stiffening zones 43 are formed of a material compatible with the material forming layer 44 for good adhesion of the layers. In a presently preferred embodiment, the material forming coextruded stiffening zones 43 softens sufficiently at temperatures suitable for blowing the layer 44 forming the balloon tubing into inflatable member 19. The coextruded zones 43 may be formed of a variety of suitable materials including polyether block amide (PEBAX) preferably having a Shore Durometer hardness of about 72D, polyamide such as nylon preferably nylon 11 and nylon 12, polyurethanes such as TECOPLAST preferably having a Shore Durometer hardness of about 82D, and polyesters such as PET, PBT, ARNITEL and HYTREL preferably having a Shore Durometer hardness of 72D or more. The layer 44 may be formed of a variety of suitable materials including polyether block amide (PEBAX), PEBAX having a Shore Durometer hardness of less than 70D, polyurethane such as PELLETHANE having a Shore Durometer hardness of not greater than 75D, and polyesters such as ARNITEL and HYTREL having a Shore Durometer hardness of less than 72 D. As illustrated in FIG. 11, the stiffening zones 43 define in part an outer most edge of the expanded balloon.

In the selectively irradiated embodiments, it may be desirable to remove the multifunctional agent from the non-crosslinked portions of the inflatable member, as many multifunctional agents can pose a health risk due to their toxicity. The multifunctional agents can be removed by selective solvent extraction, supercritical $CO_2$ extraction, or other suitable methods. If the multifunctional agent does not pose a health risk, there is generally no need to remove it.

Preferably, the soft polymers used in the invention comprise polymers having a glass transition temperature of about 20° C. to about 60° C. and more preferably up to about 37° C. to about 40° C. Specific examples include polyamide-ether block copolymer, polyether-ester block copolymer, polyester-ester block copolymer, polyester-urethane block copolymer, polyolefin, polyolefin block copolymer, polyether-urethane block copolymer. Generally, polyolefins which don't require a crosslinking agent and which lack sufficient strength for high pressure thin-walled balloons are not preferred for the formed-in-place embodiments, and polyamides are not preferred for the selectively irradiated embodiments. Suitable polymers exhibit a relatively high tensile strength of about 4000 psi to about 8000 psi, a relatively low flexural modulus of about 20,000 psi to about 75,000 psi, and a high elongation of about 300% to about 1000%, more specifically about 200% to about 500%, and preferably about 300% to about 400%. In one embodiment, the Shore durometer hardness of the polymer is about 50A to about 70D, and preferably about 60A to about 65D.

In some embodiments of the invention, it may be desirable to tailor the polymer and multifunctional agent compounds to foster crosslinking in the multifunctional material alone to form a semi-interpenetrating network (SIPN). An interpenetrating network allows the preparation of molecularly homogeneous mixtures of poorly soluble polymers. So long as the crosslinking reaction is carried out relatively quickly, the S-IPN prevents phase separation of the polymers into large domains. It is desirable to prevent phase separation as domains greater than 5 microns could act as defect points and degrade rupture and fatigue performance.

Preferably, the multifunctional agents include monomers and oligomers known in the art as crosslinking agents. Specific examples include trimethylolpropane triacrylate (TMPTA) and trimethacrylate (TMPTMA), tripropyleneglycol diacrylate (TPGDA), triallyl cyanurate (TAC), triallyl isocyanurate (TAlC), N,N'-m-phenylenediamaleimide, and trivinyl benzene.

The presently preferred radiation producing the crosslinking reaction is electron beam radiation, at a radiation dose level of about 2 Mrad to about 50 Mrad, although other suitable types of radiation, such as UV or gamma radiation may be used. Windows 18 of the mold should be configured to be substantially transparent to the type of radiation being used. Substantially transparent should be understood to mean the window should allow for greater than about 50%, preferably greater than about 70% of the radiation to pass through the window. During radiation curing of polymers, there can be competition between the desirable crosslinking reaction and oxidative chain scission. Chain scission leads to embrittlement and a loss of the growth control and dimensional stability characteristics of the invention. Accordingly, it may be desirable to add suitable antioxidants to the compounds to prevent chain scission.

While the present invention has been described herein in terms of certain preferred embodiments, modifications may be made without departing from the scope of the invention. Although individual features of embodiments of the invention may be described or shown in some of the drawings and not in others, those skilled in the art will recognize that individual features of one embodiment of the invention can be combined with any or all the features of another embodiment.

What is claimed is:

1. A balloon catheter, comprising
    a) an elongated catheter shaft; and
    b) a selectively crosslinked balloon on a distal portion of the shaft, having non-crosslinked portions, and radially spaced, longitudinally extending stiffening zones of crosslinked material along at least a section of the balloon, wherein the stiffening zones expand with adjacent portions of the balloon such that the balloon expands to a substantially cylindrical configuration.

2. The balloon catheter of claim 1 wherein the longitudinally extending stiffening zones comprise a polymeric material coextruded as an intermittent first layer of the balloon, wherein the stiffening zone polymeric material has a higher Shore durometer hardness than a polymeric material forming a second layer of the balloon.

3. The balloon catheter of claim 1, wherein the balloon comprises a polymer having a glass transition temperature of about 20° C. to about 60° C.

4. The balloon catheter of claim 3, wherein the polymer is selected from the group consisting of polyamide-ether block copolymer, polyether-ester block copolymer, polyester-ester block copolymer, polyester-urethane block copolymer, polyether-urethane block copolymer, polycarbonate-urethane block copolymer, polyolefin, and polyolefin block copolymer.

5. The balloon catheter of claim 1 wherein the longitudinally extending stiffening zones are symmetrically spaced and configured to control axial growth of the balloon during inflation thereof.

6. The balloon catheter of claim 1 wherein the stiffening zones define in part an outer most edge of the expanded balloon.

* * * * *

UNITED STATES PATENT AND TRADEMARK OFFICE
CERTIFICATE OF CORRECTION

PATENT NO. : 6,875,197 B1
DATED : April 5, 2005
INVENTOR(S) : Murthy V. Simhambhatla et al.

It is certified that error appears in the above-identified patent and that said Letters Patent is hereby corrected as shown below:

Column 3,
Line 43, delete "N,N" and insert -- N, N --.

Column 5,
Line 51, delete "cross linkable" and insert -- crosslinkable --.

Column 6,
Line 16, delete "-15" after "the".

Column 7,
Line 34, delete "N,N" and insert -- N, N --.

Signed and Sealed this

Twenty-third Day of August, 2005

JON W. DUDAS
*Director of the United States Patent and Trademark Office*